United States Patent [19]
Konishi et al.

[11] Patent Number: 5,164,412
[45] Date of Patent: Nov. 17, 1992

[54] 5-HETERO-6-OXO-PGE-DERIVATIVES

[75] Inventors: Yoshitaka Konishi; Masanori Kawamura, both of Osaka, Japan

[73] Assignee: Ono Pharmaceutical Co., Ltd., Osaka, Japan

[21] Appl. No.: 681,669

[22] Filed: Apr. 8, 1991

Related U.S. Application Data

[63] Continuation of Ser. No. 481,321, Feb. 20, 1990, abandoned.

[30] Foreign Application Priority Data

Feb. 20, 1989 [JP] Japan ................... 1-39800

[51] Int. Cl.$^5$ ................... C07C 177/00; A61K 31/557
[52] U.S. Cl. ................... 514/530; 514/19;
514/182; 514/467; 514/512; 514/513; 514/563;
549/229; 549/305; 549/454; 549/473; 552/544;
558/230; 558/276; 560/53; 560/118; 560/121;
560/122; 562/503; 562/504
[58] Field of Search ............. 560/121, 122, 118, 53;
562/503, 504; 552/544; 504/184; 558/230, 276;
549/454, 305, 473, 229; 514/19, 530, 563, 513,
182, 512, 467

[56] References Cited

U.S. PATENT DOCUMENTS

| | | | |
|---|---|---|---|
| 3,981,868 | 9/1976 | Bernady | 560/122 |
| 4,783,480 | 11/1988 | Wakatsuka | 564/189 |

OTHER PUBLICATIONS

Simonyan, Latv. PSR Zinat. Akad Vestis, Kim. Ser. (6) 735 (1988).
Bioorg. Khim., vol. 15, No. 10, 1989, pp. 1334–1340; A. Mevkh et al.
Chemical Abstracts, vol. 111 Sep. 25, 1989, p. 635, abstract No. 11490j, Columbus Ohio, US; S. P. Simonyan et al.

*Primary Examiner*—Robert Gerstl
*Attorney, Agent, or Firm*—Stevens, Davis, Miller & Mosher

[57] ABSTRACT

A Derivative of 5-hetero-6-oxo-PGE A derivative of 5-hetero-6-oxo-PGE of the formula:

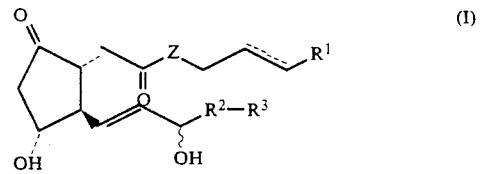

wherein R$^1$ is
(1) a group of the formula: COOR11
(2) hydroxymethylcarbonyl,
(3) hydroxymethyl or
(4) a group of the formula:

CO—AA wherein AA is an amino acid-residue,
Z is oxygen, sulfur or a group of the formula: NR21 wherein R21 is hydrogen or alkyl of C1—4;
R2 is a single-bond or alkylene of C1—4;
R3 is
  i) alkyl of C1-7,
  ii) cycloalkyl of C4-7 or cycloalkyl of C4-7 substituted by alkyl of C1-7,
  iii) phenyl, phenoxy, phenyl or phenoxy substituted by one group selected from alkyl of C1-4, halogen and trihalomethyl,===is single-bond or a double bond.

Possess PG-like activity, especially cytoprotection, and therefore are useful for treatment for and/or prevention of cytodamage.

27 Claims, No Drawings

5-HETERO-6-OXO-PGE-DERIVATIVES

This application is a continuation of application Ser. No. 481,321, filed Feb. 20, 1990 now abandoned.

FIELD OF THE INVENTION

The present invention is related to the novel derivatives of prostaglandin E.

More particularly, the present invention is related to:
1) novel derivatives of prostaglandin E of the formula:

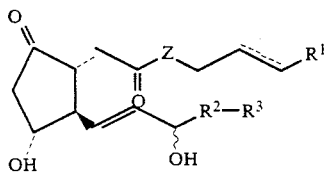

wherein all symbols are the same meaning as described hereafter,
2) the processes for the preparation of them and
3) the pharmaceutical composition containing them as active ingredient.

BACKGROUND

A prostaglandin (abbreviated to PG hereinafter) is a derivative of prostanoic acid which has the following formula:

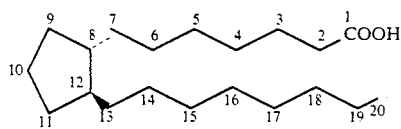

and various types of prostaglandins are known.

PG are generally known to possess pharmacological properties, for example they stimulate smooth muscle, have hypotensive, diuretic, bronchodilating, antilipolytic and antinidatory activities, and also inhibit blood platelet aggregation, gastric acid secretion and gastro-intestinal ulcers, and are, accordingly useful in the prevention and treatment of hypertension, peripheral circulatory failure, asthma, gastro-intestinal ulcers, thrombosis and myocardial infarction, in the induction of labour and abortion in pregnant female mammals and in the improvement of fertility, the control of oestrus, the contraception and the menstrual regulation in female mammals, and as diuretic agents.

RELATED ARTS

The application describing the compounds having a similar structure to the compound of the present invention of the formula (I) have described in the patent applications shown below. However each of them disclosed only the intermediates of derivatives of PGs. That is:

i) "Intermediates for Prostaglandin" in the specification of Japanese Patent Kokai No. 60-208956, i.e. European Patent Publication No. 153689, of the formula:

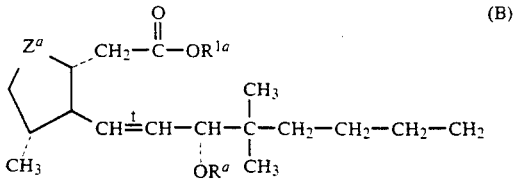

wherein Za represents C=O or

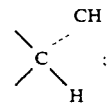

R1a and an oxygen atom to which R1a linked, together formable an ester group which is enable to hydrolize;
Ra and an oxygen atom, to which Ra linked, together formable an ether group which is enable to hydrolyze; and t means trans-configuration.

ii) "Process for the preparation of the grouping of (5E)prostaglandin E2" in the specification of Japanese Patent Kokai No. 61-56163, i.e. Derwent Acc. No. 86-115996, of the formula:

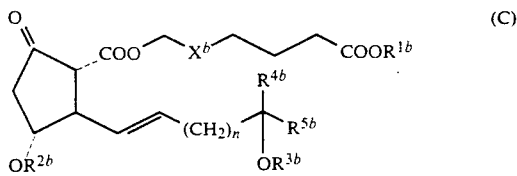

wherein R1b represents a hydrogen atom, an alkyl group of 1 to 10 carbon atom(s), a substituted or unsubstituted phenyl group, a substituted or unsubstituted cycloalkyl group of 3 to 10 carbon atom(s), or a substituted or unsubstituted phenyl alkyl (1 to 2 carbon atom(s)) group, R2b and R3b, being same or different, represent a hydrogen atom, a tri(C1-C7)-hydrocarbon silyl group, or the group forming acetal-bond together with the oxygen atom in hydroxy group, R4b represents a hydrogen atom, a methyl group, or a vinyl group, R5b represents a straight or branched alkyl group of 3 to 8 carbon atoms which may be contained oxygen atom(s); a substituted or unsubstituted phenyl group, a phenoxy group, or a cycloalkyl group of 3 to 10 carbon atoms; a straight or branched alkyl group of 1 to 5 carbon atom(s) substituted by an alkoxy group of 1 to 6 carbon atom(s), an optionally substituted phenyl group, a phenoxy group, or a cycloalkyl group of 3 to 10 carbon atoms, or Xb represents a cis-vinylene group or a trans-vinylene group, n represents an integer of 0 or 1, iii) "Process for the preparation of the grouping of (5E)prostaglandin E2" in the specification of Japanese Patent Kokai No. 62-195358, i.e. Derwent Acc. No. 87-289093, of the formula:

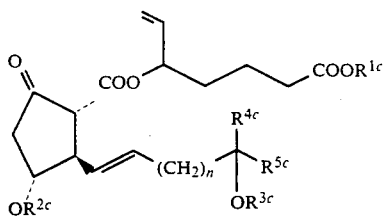

wherein R1c represent a hydrogen atom, an alkyl group of 1 to 10 carbon atom(s), a substituted or unsubstituted phenyl group, a substituted or unsubstituted cycloalkyl group of 3 to 10 carbon atoms, or a substituted or unsubstituted phenyl (C1-C2) alkyl group, R2c and R3c, being same or different, represent a hydrogen atom, a tri (C1-C7)-hydrocarbon silyl group, or a group of forming an acetal-bond together with an oxygen atom of hydroxy atom, R4c represent a hydrogen atom, a methyl group, or a vinyhl group, R5c represent a straight or branched alkyl group of 3 to 8 carbon atoms which may contain oxygen atom(s); a substituted or unsubstituted phenyl group; a substituted or unsubstituted phenoxyl group, or a substituted or unsubstituted cycloalkyl group of 3 to 10 carbon atoms; or a straight or branched alkyl group of 1 to 5 carbon atom(s) substituted by an alkoxyl group of 1 to 6 carbon atom(s), a phenyl group optionally substituted, a phenoxy group optionally substituted or a cycloalkyl group of 3 to 10 carbon atom(s) optionally substituted, n represent an integer of 0 to 1.

Recently, it was reported that new 6-keto-PGE1 wherein the 5th carbon was replaced into oxygen or imino were synthesized for the study of stereo conformation by NMR (See Chem. Abst. ref. No. 111:114900j).

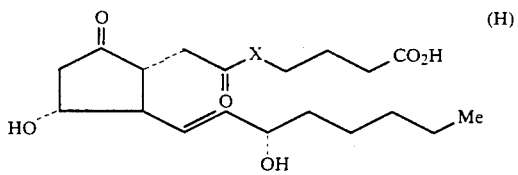

wherein X is CH2, O or NH.

Each of the aforementioned publications is incorporated herein by reference.

PURPOSE OF THE INVENTION

As the result of energetic investigations in order to find new compounds which possess the PG-like activity and have new chemical structure, the present inventors have now found that the purpose can be accomplished by the derivatives of 5-hetero-6-oxo-PGE of the formula (I), and then completed this invention.

COMPARISON WITH THE RELATED ARTS

The structure of the compounds described above under the heading "Related Arts" have a superficial similarity in structure to those of the present invention.

However all of the compounds of the prior art are disclosed as intermediates, the purpose of these being fundamentally different from the purpose of the compounds of the present invention.

For example, i) The compounds described in the specification of Japanese Patent Kokai No. 60-208956 have 5-oxa-6-oxo structure in the upper side chain (α-chain). But the purpose of the structure is for introducing trans-double bond, as intermediates, and then to obtain the final compounds of the formula:

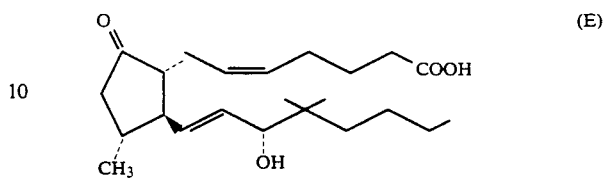

Furthermore, the substituent on 11-position of the disclosed compound is a methyl group, and is structually different from the compound of the present invention on this point.

And further, the compounds disclosed in ii) Japanese Patent Kokai No. 61-56163 and iii) Japanese Patent Kokai No. 62-195358 both are intermediates, and the analogues of PGE2 of the formula:

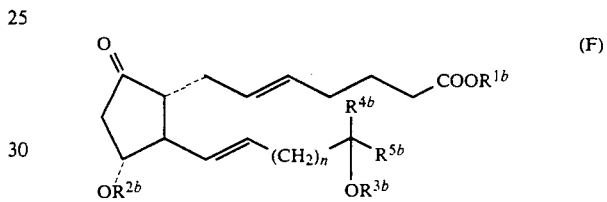

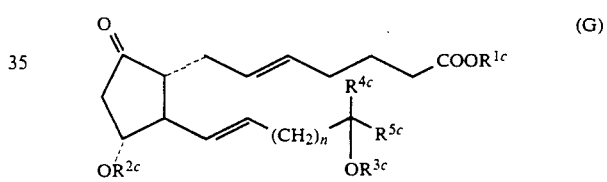

wherein each symbol is the same meaning as described hereinbefore, are final compounds.

In these intermediates, the carbonyloxy group is directly attached to the PG ring; and therefore, it is different in structure between them and the compounds of the present invention.

5-Hetero-6-keto-PGE1s of the formula (H) have the closest structure of the broadly related prior art compound as compared to the compounds of the present invention. However, the document disclosed only compounds having natural type ω-chain. And no part of the disclosure described esters.

The document mentioned only that the stereo conformation changed by the introduction of an oxygen or imino to the 5th position in the α-chain that fact dose not suggest that 5-hetero-PGE1s maintained the PG-like activity, especially cytoprotection.

Further, the 5-thia compounds were not disclosed in the above document.

SUMMARY OF THE DISCLOSURE OF THE PRESENT INVENTION

The present invention is related to the derivatives of 5-hetero-6-oxo-PGE of the formula:

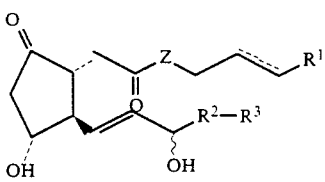

(I)

wherein R¹ is
(1) a group of the formula: COOR11 wherein R11 is
  i) hydrogen,
  ii) alkyl of C1–14,
  iii) cycloalkyl of C4–7 or cycloalkyl substituted by alkyl of C1–7.
  iv) adamantyl,
  v) a group of the formula:

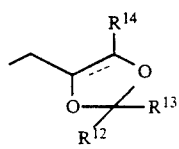

wherein R12 and R13 each, independently, is hydrogen, alkyl of C1–4 or phenyl, or R12 and R13, taken together, is oxo or a spirocyclopentane or spirocyclohexane ring, R14 is hydrogen or alkyl of C1–4, ≡≡≡ is a single-bond or a double-bond,
  vi) a group of the formula:

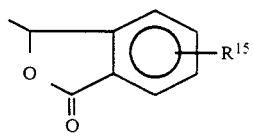

wherein R15 is hydrogen, alkyl of C1–4, halogen or trihalomethyl,
  vii) a group of the formula:

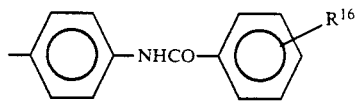

wherein R16 is hydrogen, alkyl of C1–4, halogen or trihalomethyl,
  viii) a group of the formula:

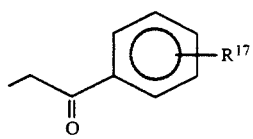

wherein R17 is hydrogen, alkyl of C1–4, halogen or trihalomethyl,
  ix) a group of the residue of steroids,
  x) alkanoyloxyalkyl of C3–10,
  xi) alkoxycarbonyloxyalkyl of C3–8,
(2) hydroxymethylcarbonyl,
(3) hydroxymethyl, or
(4) group of the formula:

CO—AA wherein AA is an amino acid-residue,
Z is oxygen, sulfur or a group of the formula: NR21 wherein R21 is hydrogen or alkyl of C1–4;
R2 is a single-bond or alkylene of C1–4;
R3 is
  i) alkyl of C1–7,
  ii) cycloalkyl of C4–7 or cycloalkyl of C4–7 substituted by alkyl of C1–7,
  iii) phenyl, phenoxy, phenyl or phenoxy substituted by one group selected from alkyl of C1–4, halogen and trihalomethyl, ≡≡≡ is single-bond or a double-bond.

With the proviso that the following compounds are excluded.
  (i) compounds wherein R2 is a single bond and R3 is phenoxy or substituted phenoxy.
  (ii) compounds wherein R1 is carboxy, Z is oxygen or imino and R2-R3 is n-pentyl; a non-toxic salt thereof or a cyclodextrin clathrate thereof.

The present invention also includes processes for the preparation of the novel derivatives as well as pharmaceutical agents containing them.

In the formula (I), alkyl of C1–14 represented by R11 means methyl, ethyl, propyl, butyl, pentyl, hexyl, heptyl, octyl, nonyl, decyl, undecyl, dodecyl, tridecyl and tetradecyl and isomers thereof.

In the formula (I), alkyl of C1–7 in R3 and R11 mean methyl, ethyl, propyl, butyl, pentyl, hexyl and heptyl and isomers thereof.

In the formula (I), alkyl of C1–4 represented by R12, R13, R14, R15, R16, R17 and R21 and in R3 mean methyl, ethyl, propyl and butyl and isomers thereof.

In the formula (I), alkyl of C1–4 represented by R2 means methylene, ethylene, trimethylene and tetramethylene and isomers thereof.

In the formula (I), cycloalkyl of C4–7 represented by R11 and in R3 means cyclobutyl, cyclopentyl, cyclohexyl and cycloheptyl groups.

In the formula (I), halogen represented by R15, R16 R17 and in R3, means fluorine, chlorine, bromine and iodine.

In the general formula (I), trihalomethyl represented by R15, R16, R17 and in R3 means methyl substituted by halogen described above.

In the formula (I), alkanoyloxyalkyl of C3–10 represented by R11 means acetyloxymethyl, isobutyloxymethyl, pivaloyloxymethyl groups etc.

In the formula (I), alkoxycarbonyloxyalkyl of C3–8 represented by R11 means methoxycarbonyloxymethyl, 1-methoxycarbonylethyl, ethoxycarbonyloxymethyl, 2-(ethoxycarbonyloxy)ethyl groups.

In the formula (I), a steroid-residue represented by R11 means the residual group of the compound having the steroid-skeleton, such as cholesterol or cholic acid, etc. wherein the hydrogen at the 3-position hydroxy group is removed.

In the formula (I), an amino acid-residue represented by AA, means the residual group wherein the hydrogen in the amino group of amino acid was removed. Amino acid above means glycine, alanine, valine, isoleucine, leucine, serine, threonine, proline, asparagine, glutamine, methionine, phenylalanine, tyrosine, aspartic acid, glutamic acid etc.

Each compound of the present invention is named as the derivative of PGE1 wherein the 5-position carbon is replaced by a hetero atom.

For example, 5-oxa-6-oxo-17S,20-dimethyl-PGE1 means a compound of the formula:

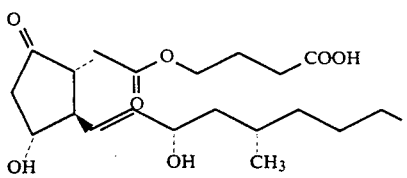

and, 5-thia-6-oxo-16-phenoxy-17,18,19,20-tetranor-1-deoxo-PGE1 means a compound of the formula:

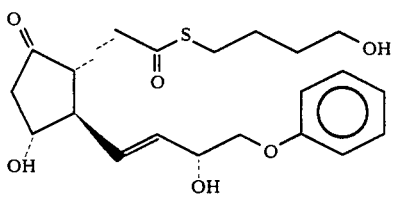

Throughout the present application, all the isomers are included unless otherwise specified. For example, alkyl, alkoxy, alkylene or alkenylene group includes straight- and branched-ones, double-bond in the alkenylene includes E, Z and EZ ones, and the present invention includes isomers occuring by the existence of asymmetric carbon atom e.g. the existence of branched alkyl.

And, as to each compound included in this specification and claims, in accordance with generally accepted rules of relative configurations, the enantiomer thereof are also included.

In each formula throughout the specification and claims, in accordance with generally accepted rules of nomenclature, the broken line (----), the thickened line (▰) and the wavy line (∼) indicate attachments in α-configuration, β-configuration or a mixture thereof, respectively.

Salts

The compounds of the formula (I) may be converted into the corresponding salts. Non-toxic and water-soluble salts are preferable. Suitable salts, for example, are as follows: salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.)

Cyclodextrin clathrates

Cyclodextrin clathrates of the PGE derivatives of the formula (I) may be prepared by the method described in Japanese Patent No. 790979 or Japanese Patent Kokai No. 47-39057, using α-, β- or γ-cyclodextrins or a mixture thereof.

Conversion into their cyclodextrin clathrates serves to increase the stability and solubility in water of the PGE derivatives of the formula (I), and is therefore useful to facilitate administration as pharmaceuticals.

Process for the preparation

The compounds of the present invention of the formula (I), that is, the compounds of the formula:

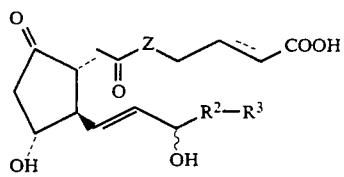

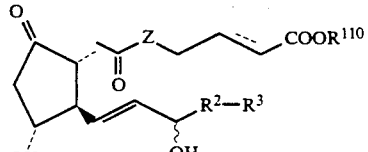

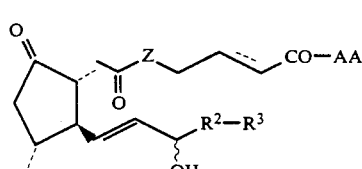

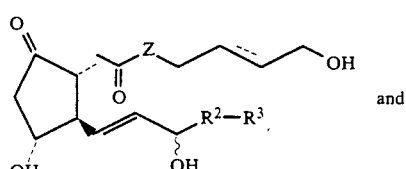

and

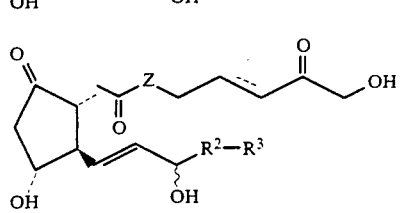

wherein each symbol in each formula has the same meaning as described hereinbefore, or represents the meaning described as follows:

R110 is
i) alkyl of C1–14,
ii) cycloalkyl of C4–7 or cycloalkyl substituted by alkyl of C1–7,
iii) adamantyl,
iv) a group of the formula:

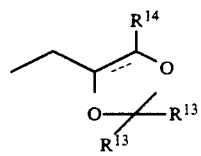

wherein R12 and R13 each, independently, is hydrogen, alkyl of C1–4 or phenyl group, or R12 and R13, taken together, is oxo or a spirocyclopentane or spirocyclohexane ring, R14 is hydrogen or alkyl of C1–4, === is a single-bond or a double-bond,
v) a group of the formula:

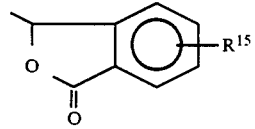

wherein R15 is hydrogen, alkyl of C1-4, halogen or trihalomethyl,
vi) a group of the formula:

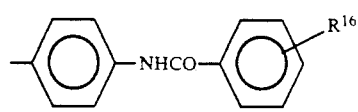

wherein R16 is hydrogen, alkyl of C1-4, halogen or trihalomethyl,
vii) a group of the formula:

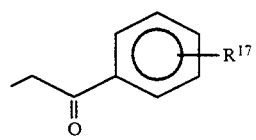

wherein R17 is hydrogen, alkyl of C1-4, halogen or trihalomethyl,
viii) a group of the residue of steroids,
ix) alkanoyloxyalkyl of C3-10,
x) an alkoxycarbonyloxyalkyl group of C3-8.
may be prepared by hydrolyzing under an acidic condition a compound of the formula:

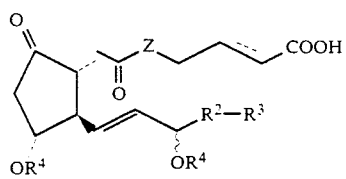 (II)

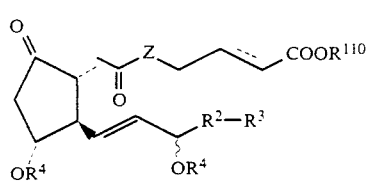 (III)

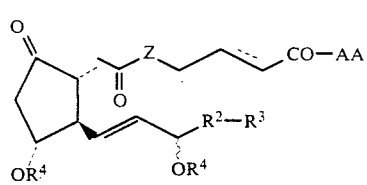 (IV)

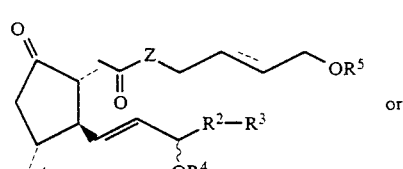 (V)

or

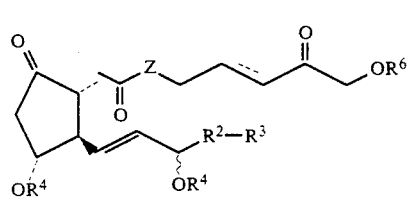 (VI)

wherein each symbol in each formula has the same meaning as described hereinbefore or represents the meaning described as follows: R4 is t-butyldimethyl-silyl, 2-tetrahydropyranyl, 2-tetrahydrofurany or 1-ethoxyethyl.

R5 is hydrogen, t-butyldimethylsilyl, 2-tetrahydropyranyl, 2-tetrahydrofuranyl or 1-ethoxyethyl. R6 is t-butyldimethylsilyl, 2-tetrahydropyranyl, 2-tetrahydrofuranyl, or 1-ethoxyethyl.

Hydrolysis in an acidic condition is known, for example, using an aqueous solution of an organic acid (acetic acid, p-toluenesulfonic acid, oxalic acid etc.) or an aqueous solution of an inorganic acid (hydrochloric acid, hydrobromic acid, sulfuric acid, phosphoric acid etc.) or a mixture thereof, in a water-miscible inert organic solvent (methanol, ethanol, THF, dioxane etc.), at a temperature of 0° C.-90° C.

Among the compounds of the formula (I), compounds of the formula:

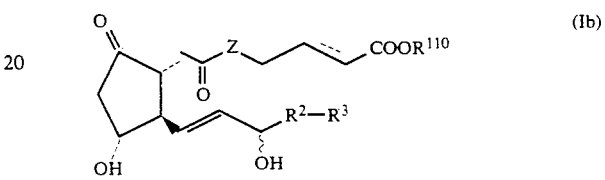 (Ib)

wherein all symbols are the same meaning as described hereinbefore.

may also be prepared by converting into esters a compound of the formula:

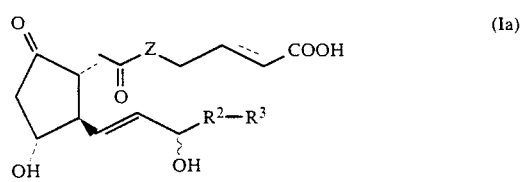 (Ia)

wherein all symbols are the same meaning as described hereinbefore.

The reaction of converting a carboxylic acid into its corresponding ester is known, for example,
1) the method of using corresponding diazoalkane,
2) the method of using corresponding alcohol
3) the method of using the compound of the general formula: R110—X wherein X is halogen and R110 is the same meaning as described hereinbefore.

Concrete description of these methods are as follows;
1) The method of using the corresponding diazoalkane, for example, may be carried out at a temperature of −10° C.-40° C., in an inert organic solvent (diethyl ether, ethyl acetate, methylene chloride etc.), using corresponding diazoalkane,
2) The method of using corresponding alcohol, for example, may be reacted in corresponding alcohol (formula: R110-OH wherein the symbol is the same meaning as described hereinbefore), in the presence of an acid (hydrochloric acid, sulfuric acid, p-toluenesulfonic acid etc.), or may be carried out at a temperature of −10° C.-40° C., in the presence of tertiary-amine (dimethylaminopyridine, diisopropylethylamine, triethylamine etc.), by using condensing agent (DCC etc.) or a halide (pivaloyl chloride or isobutyl chloroformate etc.),
3) The method of using the compound of the formula: R110—X wherein all symbols are the same meaning as described hereinbefore, may be carried out, for example, at a temperature of 10° C.-40° C., in the presence of a base (potassium fluoride etc.), by using the compound of the formula: R110—X wherein all symbols are the same meaning as described hereinbefore, in an inert organic solvent (DMF etc.).

Among the compounds of the present invention of the formula (I), compounds of the formula:

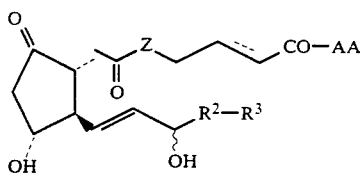

(Ic)

wherein all symbols are the same meaning as described hereinbefore.
may be prepared by reacting a compound of the formula:

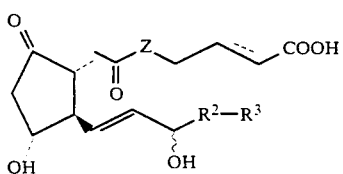

(Ia)

wherein all symbols are the same meaning as described hereinbefore.
and an amino-acid to form amide bond.

The reaction to form amide bond with a carboxylic acid and an amino acid is known, for example, 1) by using a mixed acid anhydride or
2) by using a condensing agent such as DCC Concrete descriptions of these are as follows:

1) The method using mixed acid anhydride may be carried out, for example, to react with an acid derivative (isopropyl chloroformate, ethyl chloroformate, isobutyl chloroformate etc.), in an inert organic solvent (chloroform, acetone, methylene chloride, THF etc.) or without solvent, in the presence of a tertiary amine (pyridine, triethylamine etc.) to give a mixed acid anhydride. The acid anhydride obtained is reacted with an amino acid in an inert organic solvent (the same as described hereinbefore), in the presence of alkali (sodium hydroxide solution etc.).

2) The method using a coupling agent, such as DCC, may be carried out, e.g. using the condensing agents such as DCC, in an inert organic solvent (the same as described hereinbefore), in the presence of a tertiary amine (the same as described hereinbefore).

Process for the preparation of intermediates

The intermediates for the compounds of the present invention, of the formula (II), (III), (IV), (V) and (VI) may be prepared by the known methods described in scheme (A).

Each symbol in scheme (A) has the same meaning as described hereinbefore.

Scheme (A)

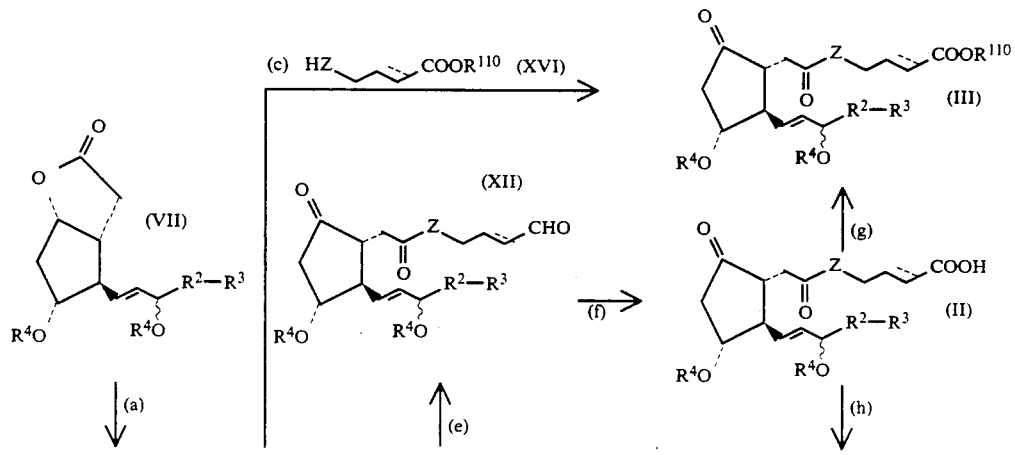

-continued
Scheme (A)

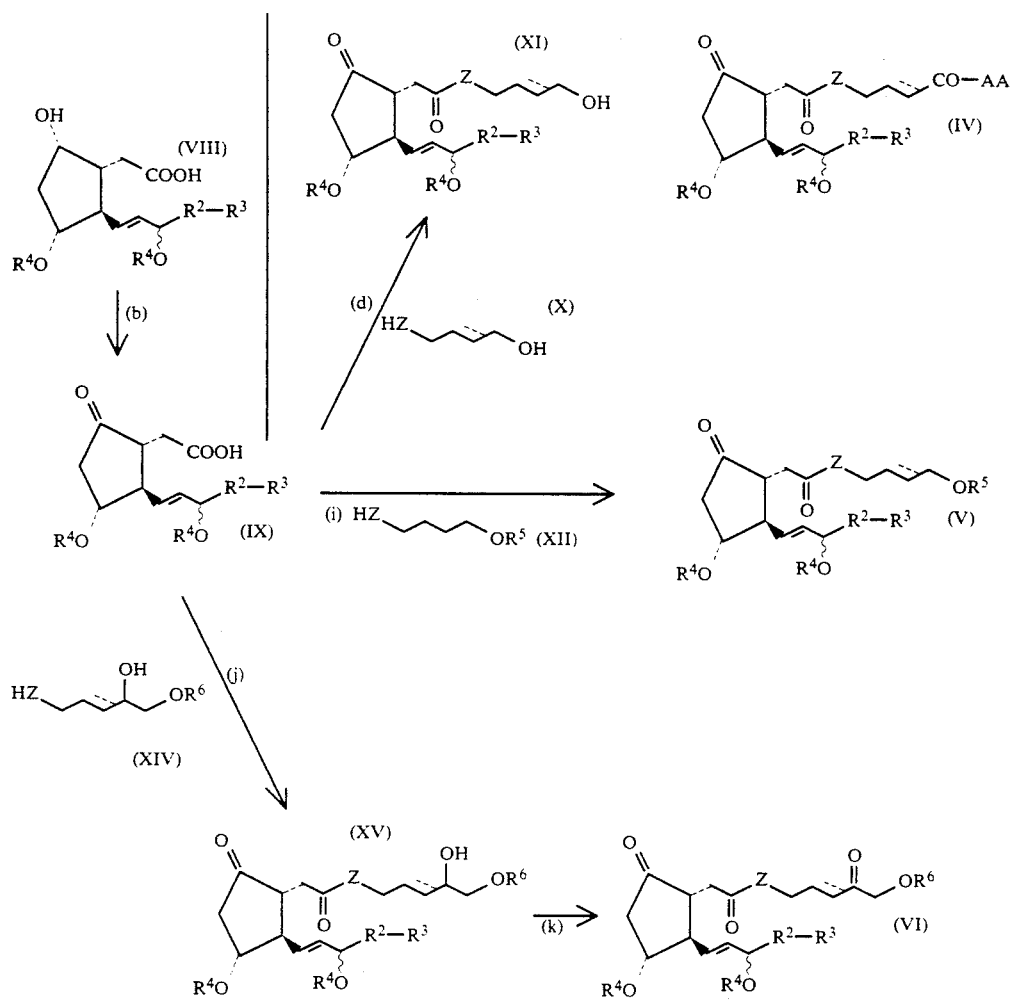

All reactions in scheme (A) are known, and may be carried out as follows.

Step <a> is ring-opening reaction of lactone, and it may be carried out, for example, by using an aqueous solution of alkali (lithium hydroxide etc.), in a water-miscible organic solvent (dimethoxyethane etc.), and the after treatment, an acid (hydrochloric acid etc.) is added to the reaction solution until neutral.

Step <b>, <f> and <k> is oxidation, it may be carried out, for example, by the method of Jone's oxidation.

Step <c>, <d>, <i> and <j> is esterification, thio-esterification or the reaction of forming amide-bond.

When Z is oxygen, for example, it may be carried out using a halogenating reagent (2-chloro-1-methylpyridinium iodide etc.), in an inert organic solvent (THF, methylene chloride etc.), in a tertiary amine (diisopropylethylamine, N,N-dimethylaminopyridine etc).

When Z is sulfur, for example, it may be carried out using a condensing agent (diphenylphosphoradiate etc.), in an inert organic solvent (DMF etc.), in the presence of a tertiary amine (triethylamine etc.).

When Z is a group of the formula: NR21 wherein all symbols are the same meaning as described hereinbefore, for example, it may be carried out using an acid derivative (isobutyl chloroformate etc.) in an alkaline condition, in an inert organic solvent (acetone etc.), in the presence of a tertiary amine (triethylamine etc.).

Step <e> is oxidation, and it may be carried out by the method of Swern oxidation. This step can be omitted.

Step <g> is esterification and it may be carried out by the same procedure of the preparation of compounds of the formula (Ib) from the compounds of the formula (Ia), described hereinbefore.

Step <h> is the reaction of forming amide-bond, and it may be carried out by the same procedure of the preparation of compounds of the formula (Ic) from the compounds of the formula (Ia), described hereinbefore.

In the reactions described in this specification, products may be purified by conventional methods, for example, distillation at atmospheric or reduced pressure, high performance liquid chromatography, thin layer or column chromatography using silica gel or magnesium silicate or by washing or recrystallization. Purification may be carried out after each reaction or after a series of reactions.

Starting Materials

The starting materials and reagents used in the preparative procedures hereinbefore described are known compounds or may be prepared by methods known per se.

For example, the compound of the formula (X) wherein Z is oxygen,=== is a single-bond is on the market.

For example, the compounds of the formula (VII) wherein R4 is 2-tetrahydropyranyl are described in Japanese Patent Kokai Nos. 47-42675, 49-117451, 50-95250, 49-109353, 50-123647 and 51-59841, i.e. Canadian Patent No. 988083, U.S. Pat. No. 4,061,865, Great Britain Patent No. 1464916, Great Britain Patent No. 1483240, Great Britain Patent No. 1464916 and Derwent Acc. No. 76-52831X, respectively. The disclosure of each of these documents is incorporated herein by reference in then entireties.

Pharmacological Activities

The compounds of the present invention of the formula (I) possess PG-like activity, described before, which has been demonstrated, for example, in a standard laboratory test. The results of such tests are as follows:

(i) Inhibitory activity on liver damage induced by carbon tetrachloride in rat (Dosage are based on weight (kg) of subject)

The compound of the present invention showed activities as in the following Table I, with the test system described hereafter.

TABLE I

| Example No. of the compound | Minimum effective dose (μg/kg) |
| --- | --- |
| 1 (a) | 50 |
| 1 (b) | 30 |
| 1 (d) | 10-30 |
| 1 (j) | 30 |
| 1 (n) | 100 |
| 1 (o) | 30 |
| 1 (p) | 30 |
| 1 (r) | 30 |
| 1 (t) | 50 |
| 1 (aa) | 30 |

Method

A solution of carbon tetrachloride (200 μl) dissolved in olive oil (10 me) was administered to Wistar male rats (body weight 190-110 g) at a rate of 2000 μl/kg animal body weight by intraperitoneal injection.

A solution of a compound of the present invention in olive oil (2 mg/kg animal body weight) was administered three times, at the same time, 6 hrs and 12 hrs after the dosage of carbon tetrachloride. Blood was collected twice, 24 hrs after and 48 hrs after the first dosage. The blood was centrifuged and plasma GOT (glutamic oxalacetic transaminase) activity and plasma GPT (glutamic pyruvic transaminase) activity were measured. The minimum effective dose shown as the minimum dose which had a significant effect on the plasma GOT and GPT levels.

(ii) Hypotensive activity in dog

The compound of the present invention showed hypotensive activities as the following Table II, with the test system described hereafter.

TABLE II

| Example No. of the compound | Effective dose (μg/kg) |
| --- | --- |
| 1 (b) | 42 |
| 1 (d) | 17 |

TABLE II-continued

| Example No. of the compound | Effective dose (μg/kg) |
| --- | --- |
| 1 (f) | 40 |
| 1 (g) | 83 |
| 1 (i) | 125 |
| 1 (j) | 16 |
| 1 (n) | 20 |
| 1 (o) | 40 |
| 1 (p) | 140 |
| 1 (r) | 20 |
| 1 (aa) | 5 |

Method

Mongrel dogs weighing 8-12 kg were used. The animals were anesthetized with pentobarbital sodium. A polyethylene tube was canulated into femoral artery and a silastic tube was canulated into duodenum. Both tubes were pulled through a subcataneous tunnel and out of a skin incision made on the back.

The animals were restrained in steel stand under non-anesthesia and systemic blood pressure were measured via fermoral arterial catheter. The compounds of the present invention were administered into duodenum via duodenal catheter. Effective dose showed the decrease of 20 mmHg.

(iii) Diarrhea in dog

The compounds of the present invention had the diarrhea effect on oral administration dose showed in the following Table III.

TABLE III

| Example No. of the compound | Occurence dose (μg/kg) |
| --- | --- |
| 1 (a) | 300 |
| 1 (b) | 100 |
| 1 (d) | 100 |
| 1 (j) | 100 |
| 1 (n) | >100 |
| 1 (o) | 100 |
| 1 (p) | 100 |
| 1 (r) | 100 |
| 1 (t) | 1000 |
| 1 (aa) | 30 |

Toxicity

The toxicity of the compounds of the present invention is very low and compounds of the present invention may be considered to be sufficiently safe and suitable for pharmaceutical use.

Application for the Pharmaceuticals

For use, in the treatment and/or prevention of vasodilative action, antihypertensive agent, angina pectoris cardiac infarction, thrombosis, arteriosclerosis and cytodamage, the derivatives of prostaglandin E of the formula (I) or non-toxic salts thereof or cyclodextrin clathrates thereof will normally be administered systemically or partially, usually by oral or parenteral administration.

And the derivatives of prostaglandin E of the formula (I) have strong effect of cytoprotection, and thus are useful for the treating agent of cytodamage.

That is, the derivatives of prostaglandin E of the formula (I) or non-toxic salts thereof or cyclodextrin clathrates thereof or are useful for the treatment and/or prevention of diseases induced by cytodamage, for example, (1) digestive system diseases (e.g. liver disease such as hepatitis fatty liver, liver cirrhosis, liver abscess and pancreatic disease such as pancreatitis.)
(2) urologic diseases (e.g. nephritis, diabetic nephropathies, crystitis and urethritis),
(3) respiratory tract diseases (e.g. pneumonia, empyema and rhinitis),
(4) cardiovascular diseases (e.g. arrhythmia, cerebral aneurysm and cerebral embolism)
(5) haemotologic diseases (e.g. anemia)
(6) other diseases (e.g. diabetes mellitus and complications caused by diabetes mellitus)

The dose to be administered is determined depending upon age, body weight, symptom, the desired therapeutic effect, the route of administration, and the duration of the treatment etc. In the human adult, the doses per person for one time are generally between 0.1 μg and 100 μg, by oral administration up to several times per day, and between 0.01 μg and 50 μg, by parenteral administration (preferably by intravenous administration) up to several times per day.

As mentioned above, the doses to be used depend on various conditions. Therefore, there are cases in which doses lower than the ranges specified above and doses greater than the ranges specified above, may be used.

Solid compositions according to the present invention for oral administration include compressed tablets, dispersible powders and granules. In such solid compositions, one or more of the active compound(s) is or are, admixed with at least one inert diluent such as lactose, mannitol, glucose, hydroxypropylcellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, and, disintegrating agents such as cellulose calcium glycolate. The tablets or pills may, if desired, be made into gastric film-coated or enteric film-coated tablets or pills, such as sugar-coated, gelatin-coated, hydroxypropylcellulose-coated or hydroxypropylmethylcellulose phthlate-coated tablets or pills; two or more layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions. Examples of aqueous solvents or suspending media are distilled water for injection and physiological salt solutions. Examples of non-aqueous solvents or suspending media are propylene glycol, polyethylene glycol, vegetable oils, such as olive oil, alcohols such as ethanol, Polysorbate 80 (registered Trade Mark). These compositions may also include adjuvants such as preserving, wetting, emulsifying and dispersing agents, stabilizing agents (e.g. lactose) and solubilizing agents (e.g. glutamic acid, aspartic acid).

They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories for rectal administration and pessaries which comprise one or more of the active compound(s) and may be prepared by known methods.

REFERENCE EXAMPLE AND EXAMPLE

The following Reference Examples and Examples illustrate the preparation of compounds of the present invention, however, the present invention is not restricted by them.

The solvents in the parentheses show the developing or eluting solvents and the ratios of the solvents used are by volume in chromatographic separation.

Unless otherwise specified, "IR" were measured by liquid film method.

REFERENCE EXAMPLE 1

Synthesis of 11,15-O-bis(tetrahydropyran-2-yl)-17S,20-dimethyl-2,3,4,5,6-pentanor-PGF1

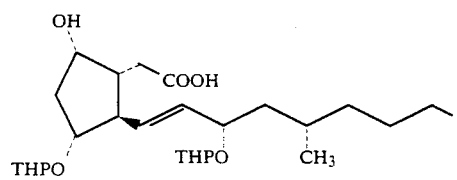

The mixture of 2-oxa-3-oxo-6-syn-[5S-methyl-3S-(tetrahydropyran-2-yloxy)-non-1E-enyl]-7-anti-(tetrahydropyran-2-yloxy)-cis-bicyclo[3,3,0]octane (20 g), 1N lithium hydroxide (86 ml) and dimethoxyethane (100 ml) was stirred for 40 minutes at room temperature, and the reaction mixture was poured into ice-cooled 1N-hydrochloric acid. Organic layer separated and the extract with EtOAc was washed, dried and evaporated to give the title compound (19 g).

REFERENCE EXAMPLE 2

Synthesis of 11,15-O-bis(tetrahydropyran-2-yl)-17S,20-dimethyl-2,3,4,5,6-pentanor-PGE1

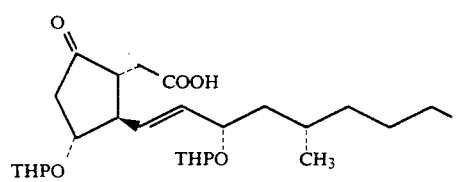

A solution of the compound prepared in reference example 1 (19 g) in acetone (200 ml) was to cooled to −30° C., and Jone's reagent (2.7N; large excess) was added dropwise to the solution over a period of 30 minutes. Reaction solution was stirred for 1.5 hours at −20° C. Isopropyl alcohol was added to this solution and the mixture was vigorously stirred.

Ice-water and ether are added to the reaction mixture, and the mixture was stirred. The oily layer was washed with successive, water and a saturated aqueous solution of sodium chloride. The solution was dried and evaporated to give the title compound (19 g) having the following physical data.

IR: ν2931, 1747, 1455, 1376, 1242, 1201, 1133, 1078, 1023, 974, 912, 870, 815 cm−1.

REFERENCE EXAMPLE 3

Synthesis of 11,15-O-bis(tetrahydropyran-2-yl)-17S,20-dimethyl-5-oxa-6-oxo-1-deoxo-PGE1.

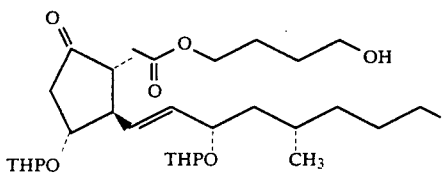

The mixture of the compound prepared in reference example 2 (19 g), butanediol (76 ml), 2-chloro-1-methylpyridium iodide (19.8 g), diisopropylethylamine (27 ml), N,N-dimethylaminopyridine (263 mg) and THF (400 ml) was stirred for 1 hour at room temperature. The reaction mixture was diluted with EtOAc, the diluted solution was washed with successive, dil. hydrochloric acid, an aqueous solution of sodium bicarbonate, water and a saturated aqueous solution of sodium chloride, dried and evaporated. The residue was purified by column chromatography on silica gel to give the title compound (19.5 g) having the following physical data.

TLC: Rf 0.26 (EtOAc:hexane=1:1)

REFERENCE EXAMPLE 4

Synthesis of 11,15-O-bis(tetrahydropyran-2-yl)-17S,20-dimethyl-5-oxa-6-oxo-1-dehydroxy-PGE1

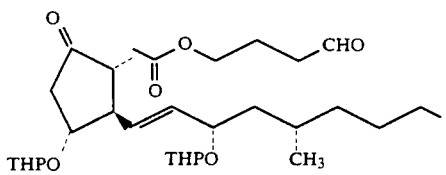

In an atmosphere of argon, a solution of dimethyl sulfoxide (0.28 ml) in methylene chloride (1 ml) was added to a solution of oxalyl chloride (0.16 ml) in methylene chloride (5 ml) at −78° C., and the mixture was stirred for 30 minutes at the same temperature.

The solution of the compound prepared in reference example 3 (633 mg) in methylene chloride (4 ml) was added to the solution slowly, and the mixture was stirred for 1 hour at −78° C. Triethylamine (0.88 ml) was added to the reaction solution. The solution was stirred and temperature of the solution was gradually raised to 0° C. over a period of 1 hour. Water (10 ml) was added to the reaction mixture, and the mixture was extracted with ether. The oily layer was washed with successive, water and a saturated aqueous solution of sodium chloride. The solution was dried and evaporated to give the title compound (633 mg) having the following physical data.

TLC: Rf 0.49 (EtOAc:hexane=1:1)

REFERENCE EXAMPLE 5

Synthesis of 11,15-O-bis(tetrahydropyran-2-yl)-17S,20-dimethyl-5-oxa-6-oxo-PGE1

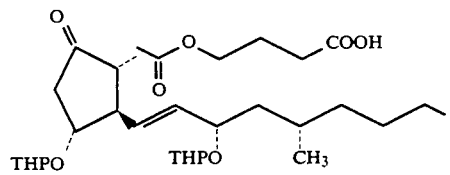

The solution of the compound prepared in reference example 4 (633 mg) in acetone (10 ml) was cooled to −20° C., and Jone's reagent (2.6N; 1.5 ml) was added to the solution dropwise, the mixture was stirred for 30 minutes at the same temperature. Isopropyl alcohol (1 ml) was added to the reaction solution, and ether and water were added. The organic layer was washed with successive, water and a saturated aqueous solution of sodium chloride. The solution was dried and evaporated. The residue was purified by column chromatography on silica gel to give the title compound (572 mg) having the following physical data.

TLC: Rf 0.15 (EtOAc:hexane=2:1);
IR: 1735, 1350, 1125, 1075, 1020, 975 cm−1.

REFERENCE EXAMPLE 6

Synthesis of 11,15-O-bis(tetrahydropyran-2-yl)-17S,20-dimethyl-PGE1 methyl ester

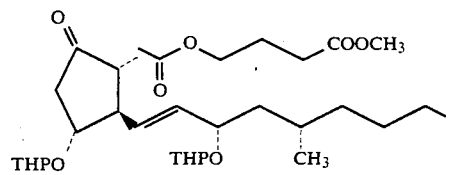

The solution of diazomethane in ether was added dropwise to the solution of the compound prepared in reference example 5 (360 mg) in EtOAc (10 ml) at 0° C. After the reaction, the reaction solution was evaporated to give the title compound (365 mg).

REFERENCE EXAMPLE 7

Synthesis of 11,15-O-bis(tetrahydropyran-2-yl)-17S,20-dimethyl-5-aza-6-oxo-PGE1

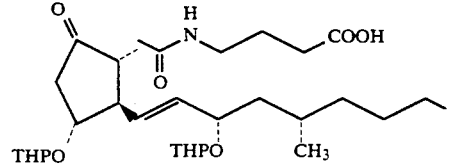

The solution of the compound prepared in reference example 2 (482 mg) in anhydrous acetone (5 ml) was cooled to −15° C., triethylamine (153 ml) and isobutyl chloroformate (143 ml) were added dropwise to the solution, the mixture was stirred for 15 minutes at the same temperature.

The suspension of γ-aminobutanoic acid (206 mg) in acetone (8 ml) was cooled with ice, a 0.5N aqueous solution of sodium hydroxide (4 ml) was added to the solution.

The filtrate of the solution of mixed anhydride prepared above by glass filter was added to the mixture, the mixture was stirred for 20 minutes, cooling with water. 1N hydrochloric acid was added to the reaction solution, the mixture was extracted with EtOAc. The oily layer was washed with a saturated aqueous solution of sodium chloride, dried and evaporated. The residue was purified by column chromatography on silica gel (EtOAc-hexane) to give the title compound (380 mg) having the following physical data.

TLC: Rf 0.19 (EtOAc:methanol=9:1)

REFERENCE EXAMPLE 8

Synthesis of 11,15-O-bis(tetrahydropyran-2-yl)-17S,20-dimethyl-5-oxa-6-oxo-2-[1-hydroxy-2-(tetrahydropyran-2-yloxy)ethyl]-2-decarboxy-PGE1

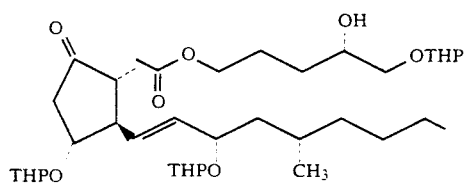

Chloro-1-methylpyridium iodide (261 mg), trimethylamine (286 μl), 1,2,5-trihydroxypentane 1-tetrahydropyranyl ether (348 mg) and N,N-dimethylaminopyridine (catalytic amount) were added to a solution of the compound prepared in reference example 2 (410 mg) in methylene chloride (30 ml), and the mixture was stirred for 1 hour at room temperature. After the reaction, 1N hydrochloric acid and EtOAc were added to the reaction solution. The oily layer was washed, dried and evaporated. The residue was purified by column chromatography on silica gel (EtOAc:hexane=1:1) to give the title compound (314 mg).

REFERENCE EXAMPLE 9

Synthesis of 11,15-O-bis(tetrahydropyran-2-yl)-17S,20-dimethyl-5-oxa-6-oxo-2-[2-(tetrahydropyran-2-yloxy)ethanoyl]-2-decarboxy-PGE1

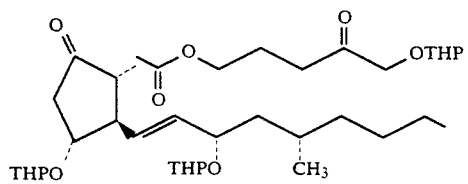

Pyridium dichlorochromate (442 mg) was added to the solution of the compound prepared in reference example 8 (314 mg) in DMF (3 ml), the mixture was stirred for 3 days. The reaction solution was filtered, and the filtrate was purified by column chromatoglaphy on silica gel (EtOAc:hexane=2:3) to give the title compound (191 mg).

REFERENCE EXAMPLE 10

Synthesis of 11,15-O-bis(tetrahydropyran-2-yl)-17S,20-dimethyl-5-thia-6-oxo-PGE1 methyl ester

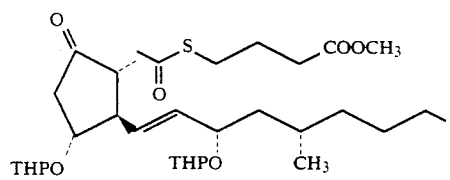

Triethylamine (384 mg) was added to a solution of the compound prepared in reference example 2 (600 mg) and diphenyl phosphoradiate (378 mg) in DMF (6 ml), the mixture was stirred for 30 minutes. Methyl 4-mercaptbutanoate (252 mg) was added to this solution, the mixtures was stirred overnight. After the reaction, water and EtOAc were added to the reaction solution. The oily layer was washed, dried and purified by column chromatography on silica gel (EtOAc:hexane=35:65) to give the title compound (520 mg) having the following physical data.

IR: ν 2930, 1745, 1690, 1440, 1375, 1320, 1200, 1135, 1080, 1035, 975, 910 cm−1.

REFERENCE EXAMPLE 11

Synthesis of 11,15-O-bis(tetrahydropyran-2-yl)-17S,20-dimethyl-5-oxa-6-oxo-PGE1 N-(1S-carboxy-3-methyl)butylamide

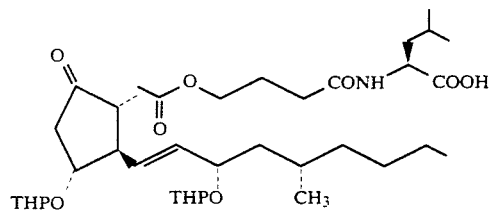

Triethylamine (0.11 ml) and isobutyl chloroformate (0.1 ml) were added dropwise to a solution of the compound prepared by reference example 5 (270 mg) in acetone (3.5 ml) at −15° C., the mixture was stirred for 20 minutes at the same temperature. A 0.5N aqueous solution of sodium hydroxide (2.72 ml) was added dropwise to the suspension of L-leucine (179 mg) in acetone (5.4 ml) at −10° C., the mixture was stirred for 5 minutes. The mixed anhydride solution through glass filter was added to the reaction solution, the mixture was stirred for 30 minutes at −10° C. 1N hydrochloric acid (2ml) was added to the reaction solution, the mixture was extracted with EtOAc. Oily layer was washed, dired and evaporated. The residue was purified by column chromatography on silica gel (EtOAc-hexane) to give the title compound (310 mg) having the following physical data.

TLC: Rf 0.30 (EtOAc:acetic acid=98:2).

EXAMPLE 1

Synthesis of
5-oxa-6-oxo-17S,20-dimethyl-1-deoxo-PGE1

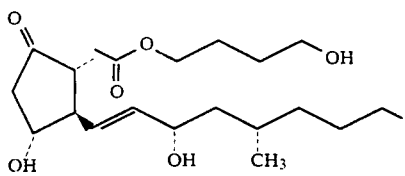

65% acetic acid (5 ml) was added to a solution of the compound prepared in reference example 3 (320 mg) in THF (0.5 ml), the mixture was stirred for 2 hours at 45° C. Ice water and EtOAc were added to the reaction mixture. The oily layer separated was washed with successive, water and a saturated aqueous solution of sodium chloride, dried, and evaporated. The residue was purified by column chromatography on silica gel (EtOAc-methanol) to give the title compound (150 mg) having the following physical data.

TLC: Rf 0.35 (EtOAc:methanol=20:1);
IR: $\nu$ 3500–3250, 2970–2850, 1720 cm−1.

EXAMPLE 1(a)–1(II)

By the same method shown in Reference Example 1 to 11 and by the same procedure of Example 1, the compound having the physical data described in following Table IV, V, VI and VII were given.

TABLE IV

[Structure: cyclopentanone core with =O, -OH, lactone ring with -R¹ substituent and -R²-R³ side chain with OH]

| Example No. | —R¹ (alkene group) | —R²—R³ | Name | TLC | mp or IR | Reference examples used |
|---|---|---|---|---|---|---|
| 1 (a) | [alkenyl] | [chain with OH, ethyl branch] | 5-oxa-6-oxo-16S,18S-ethano-20-ethyl-1-deoxo-PGE₁ | Rf 0.48 (EtOAc:CH₃OH = 20:1) | mp: 70~71° C. | 1, 2, 3 |
| 1 (b) | [alkenyl-COOH] | [chain with CH₃] | 5-oxa-6-oxo-17S,20-dimethyl-PGE₁ | Rf 0.27 (EtOAc:acetic acid = 99:1) | IR: ν 3400, 1720, 1400, 1240, 1160, 1075, 970 cm⁻¹ | 1, 2, 3, 4, 5 |
| 1 (c) | [cholesteryl ester group] | [chain with CH₃] | 5-oxa-6-oxo-17S,20-dimethyl-PGE₁ cholesterol ester | Rf 0.23 (EtOAc:hexane = 2:1) | IR(CHCl₃Solution): ν 3450, 1730, 1635, 1455, 1315, 1160, 1070 cm⁻¹ | 1, 2, 3, 4, 5, 6 |
| 1 (d) | [alkenyl-COOCH₃] | [chain with CH₃] | 5-oxa-6-oxo-17S,20-dimethyl-PGE₁ methyl ester | Rf 0.15 (EtOAc:hexane = 2:1) | IR: ν 3400, 2920, 1730, 1715, 1430, 1350, 1240, 1160, 1070 cm⁻¹ | 1, 2, 3, 4, 5, 6 |

TABLE IV-continued

| Example No. | $-R^2-R^3$ | $R^1$ | Name | TLC | mp or IR | Reference examples used |
|---|---|---|---|---|---|---|
| 1 (e) | COO-C6H4-NHC(O)C6H5 | CH(CH3)-C2H5 chain | 5-oxa-6-oxo-17S,20-dimethyl-PGE1 4-(benzoylamino)phenyl ester | Rf 0.23 (CHCl3:THF:acetic acid = 10:2:1) | IR: ν 3470, 3350, 2940, 1750, 1730, 1650, 1610, 1525, 1410, 1360, 1315, 1190, 1165, 1145, 1070 cm$^{-1}$ | 1, 2, 3, 4, 5, 6 |
| 1 (f) | COO-cyclohexyl | CH(CH3)-C2H5 chain | 5-oxa-6-oxo-17S,20-dimethyl-PGE1 cyclohexyl ester | Rf 0.57 (EtOAc) | IR: ν 3450, 2910, 2850, 1720, 1440, 1350, 1240, 1160, 1070, 1030, 1010, 960 cm$^{-1}$ | 1, 2, 3, 4, 5, 6 |
| 1 (g) | COO-n-C10H21 | CH(CH3)-C2H5 chain | 5-oxa-6-oxo-17S,20-dimethyl-PGE1 decyl ester | Rf 0.68 (EtOAc) | IR: ν 3400, 2950, 2920, 2860, 1730, 1450, 1350, 1240, 1160, 1080, 1000, 960 cm$^{-1}$ | 1, 2, 3, 4, 5, 6 |
| 1 (h) | COO-CH(CH3)2 | CH(CH3)-C2H5 chain | 5-oxa-6-oxo-17S,20-dimethyl-PGE1 isopropyl ester | Rf 0.12 (EtOAc:hexane = 2:1) | IR: ν 3410, 2930, 1730, 1460, 1380, 1250, 1170, 1105, cm$^{-1}$ | 1, 2, 3, 4, 5, 6 |

TABLE IV-continued

| Example No. | —R²—R³ | Name | TLC | mp or IR | Reference examples used |
|---|---|---|---|---|---|
| 1 (i) | (adamantyl ester group) | 5-oxa-6-oxo-17S,20-dimethyl-PGE₁ adamantyl ester | Rf 0.16 (EtOAc:hexane = 2:1) | IR: ν 3390, 2900, 1720, 1450, 1350, 1235, 1160, 1070, 1040 cm⁻¹ | 1, 2, 3, 4, 5, 6 |
| 1 (j) | (pivaloyloxymethyl ester) | 5-oxa-6-oxo-17S,20-dimethyl-PGE₁ pivaloyloxymethyl ester | Rf 0.35 (EtOAc) | IR: ν 3360, 2920, 1725, 1450, 1400, 1355, 1150, 1110, 1080, 1020, 980 cm⁻¹ | 1, 2, 3, 4, 5, 6 |
| 1 (k) | (methyl ester, 2,3-dehydro) | 5-oxa-6-oxo-17S,20-dimethyl-2,3-dehydro-PGE₁ methyl ester | Rf 0.33 (EtOAc) | IR: ν 3400, 1745, 1670, 1160 cm⁻¹ | 1, 2, 3, 4, 5, 6 |
| 1 (l) | (2,2-dimethyl-1,3-dioxoran-4-ylmethyl ester) | 5-oxa-6-oxo-17S,20-dimethyl-PGE₁ 2,2-dimethyl-1,3-dioxoran-4-ylmethyl ester | Rf 0.28 (EtOAc) | IR: ν 3441, 2928, 1741, 1373, 1171, 1084 cm⁻¹ | 1, 2, 3, 4, 5, 6 |

TABLE IV-continued

| Example No. | —R²—R³ | Name | TLC | mp or IR | Reference examples used |
|---|---|---|---|---|---|
| 1 (m) | (ethyl carbonate ester structure with CH₃ branch) | 5-oxa-6-oxo-17S,20-dimethyl-PGE₁ 1-(ethoxycarbonyloxy)-ethyl ester | Rf 0.50 (EtOAc) | IR: ν 3856, 3809, 3738, 3401, 2959, 2928, 2873, 2363, 1747, 1449, 1393, 1375, 1269, 1163, 1078 cm⁻¹ | 1, 2, 3, 4, 5, 6 |
| 1 (n) | (5-methyl-2-oxo-1,3-dioxolen-4-ylmethyl ester structure with CH₃ branch) | 5-oxa-6-oxo-17S,20-dimethyl-PGE₁ 5-methyl-2-oxo-1,3-dioxolene-4-ylmethyl ester | Rf 0.38 (EtOAc) | IR: ν 3401, 2958, 2927, 2873, 1822, 1746, 1545, 1392, 1358, 1305, 1230, 1196, 1161, 1083, 1046, 1014 cm⁻¹ | 1, 2, 3, 4, 5, 6 |
| 1 (o) | (3-phthalidyl ester structure with CH₃ branch) | 5-oxa-6-oxo-17S,20-dimethyl-PGE₁ 3-phthalidyl ester | Rf 0.41 (EtOAc) | IR: ν 3401, 2957, 2927, 2872, 1788, 1745, 1679, 1413, 1358, 1311, 1287, 1242 cm⁻¹ | 1, 2, 3, 4, 5, 6 |

TABLE IV-continued

| Example No. | —R²—R³ / R¹ | Name | TLC | mp or IR | Reference examples used |
|---|---|---|---|---|---|
| 1(p) | R² = -CH₂-COO-CH₂-C(O)-C₆H₄-Br (4-bromo); R³ = -CH(CH₃)-C₅H₁₁ (heptyl chain with 17S,20-dimethyl) | 5-oxa-6-oxo-17S,20-dimethyl-PGF₁ 4-bromobenzoylmethyl ester | Rf 0.50 (EtOAc) | mp: 49~50° C. | 1, 2, 3, 4, 5, 6 |
| 1(q) | R² = -CH₂-COO-CH₂-C(O)-C₆H₅; R³ = -CH(CH₃)-C₅H₁₁ | 5-oxa-6-oxo-17S,20-dimethyl-PGF₁ benzoylmethyl ester | Rf 0.34 (EtOAc) | IR: ν 3400, 2927, 1747, 1704, 1636, 1599, 1451, 1419, 1375, 1230, 1168, 1078, 971 cm⁻¹ | 1, 2, 3, 4, 5, 6 |
| 1(r) | R² = -(CH₂)₄-COOC₂H₅; R³ = -CH(CH₃)-C₅H₁₁ | 5-oxa-6-oxo-17S,20-dimethyl-PGF₁ ethyl ester | Rf 0.38 (EtOAc) | IR: ν 3810, 3401, 2959, 2927, 2873, 1739, 1464, 1394, 1376, 1354, 1250, 1180, 1083, 1036 cm⁻¹ | 1, 2, 3, 4, 5, 6 |
| 1(s) | R² = -(CH₂)ₙ-CONH-CH(COOH)-CH₂-CH(CH₃)₂; R³ = -CH(CH₃)-C₅H₁₁ | 5-oxa-6-oxo-17S,20-dimethyl-PGE₁ N-(1S-carboxyl-3-methyl)butylamide | Rf 0.32 (EtOAc:CH₃OH:acetic acid = 90:20:1) | IR(CHCl₃ solution): ν 3428, 1735, 1636, 1515, 1318 cm⁻¹ | 1, 2, 3, 4, 5, 11 |

TABLE IV-continued

| Example No. | —R²—R³ | Name | TLC | mp or IR | Reference examples used |
|---|---|---|---|---|---|
| 1 (t) | COOH (straight chain) | 5-oxa-6-oxo-16S,18S-ethano-20-ethyl-PGE₁ | Rf 0.36 (EtOAc:formic acid = 80:1) | mp: 96~98° C. | 1, 2, 3, 4, 5 |
| 1 (u) | COOCH₃ (with branched ethyl) | 5-oxa-6-oxo-16S,18S-ethano-20-ethyl-PGE₁ methyl ester | Rf 0.24 (EtOAc) | mp: 75~76° C. | 1, 2, 3, 4, 5, 6 |
| 1 (v) | COOCH₃ (with phenoxy) | 5-oxa-6-oxo-16-phenoxy-17,18,19,20-tetranor-PGE₁ methyl ester | Rf 0.34 (EtOAc) | IR: ν 3446, 3063, 2954, 2927, 1733, 1600, 1588, 1496, 1456, 1439, 1394, 1373, 1294, 1246, 1196, 1173, 1081, 1042 cm⁻¹ | 1, 2, 3, 4, 5, 6 |
| 1 (w) | COOCH₃ (with CF₃-phenoxy) | 5-oxa-6-oxo-16-(3-trifluoromethyl)phenoxy-17,18,19,20-tetranor-PGE₁ methyl ester | Rf 0.33 (EtOAc) | IR: ν 3441, 2956, 1740, 1593, 1494, 1451, 1395, 1332, 1296, 1243, 1169, 1126, 1097, 1068, 1037 cm⁻¹ | 1, 2, 3, 4, 5, 6 |
| 1 (x) | glycoloyl group with CH₃ branch | 5-oxa-6-oxo-17S,20-dimethyl-2-glycoloyl-2-decarboxy-PGE₁ | Rf 0.14 (EtOAc) | IR: ν 3368, 2959, 2922, 2287, 1748, 1732, 1715, 1463, 1403, 1378, 1244, 1201, 1162, 1077, 1049 cm⁻¹ | 1, 2, 8, 9 |

TABLE IV-continued
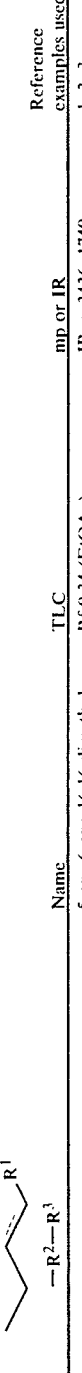
| Example No. | −R²−R³ | Name | TLC | mp or IR | Reference examples used |
|---|---|---|---|---|---|
| 1(y) | 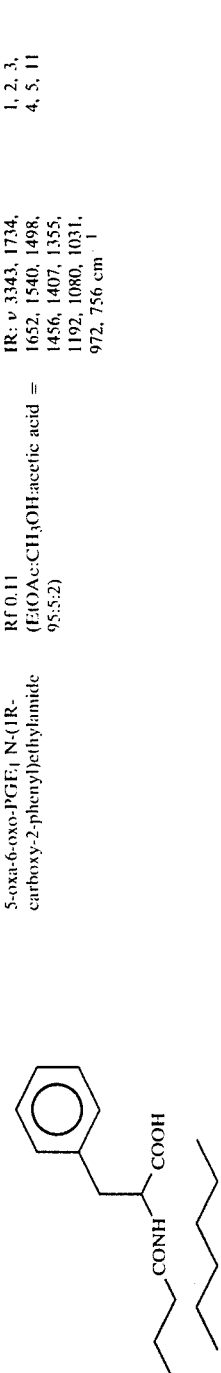 COOCH₃ with H₃C-C(CH₃)- group | 5-oxa-6-oxo-16,16-dimethyl-PGE₁ methyl ester | Rf 0.34 (EtOAc) | IR: ν 3436, 1740, 1439, 1364, 1245, 1174, 1083, 1046 cm⁻¹ | 1, 2, 3, 4, 5, 6 |
| 1(z) | benzyl-CH(CONH-)COOH | 5-oxa-6-oxo-PGE₁ N-(1R-carboxy-2-phenyl)ethylamide | Rf 0.11 (EtOAc:CH₃OH:acetic acid = 95:5:2) | IR: ν 3343, 1734, 1652, 1540, 1498, 1456, 1407, 1355, 1192, 1080, 1031, 972, 756 cm⁻¹ | 1, 2, 3, 4, 5, 11 |

TABLE V

| Example No. | ⌒⌒R¹ / —R²—R³ | Name | TLC | mp or IR | Reference examples used |
|---|---|---|---|---|---|
| 1 (aa) | ⌒⌒⌒COOCH₃ / ⌒⌒⌒⌒ (CH₃) | 5-thia-6-oxo-17S,20-dimethyl-PGE₁ methyl ester | Rf 0.38 (EtOAc) | IR: $\nu$  3369, 2927, 1747, 1687, 1438, 1376, 1319, 1239, 1077, 972 cm⁻¹ | 1, 2, 10 |
| 1 (bb) | ⌒⌒⌒COOCH₃ / ⌒O-Ph | 5-thia-6-oxo-16-phenoxy-17,18,19,20-tetranor-PGE₁ methyl ester | Rf 0.38 (EtOAc) | IR: $\nu$  3401, 2927, 1741, 1685, 1600, 1496, 1438, 1245, 1174, 1041, 889, 758, 694 cm⁻¹ | 1, 2, 10 |
| 1 (cc) | ⌒⌒⌒COOCH₃ / ⌒⌒⌒⌒ | 5-thia-6-oxo-16S,18S-ethano-20-ethyl-PGE₁ methyl ester | Rf 0.40 (EtOAc) | mp: 92~93° C. | 1, 2, 10 |
| 1 (dd) | ⌒⌒⌒COOCH₃ / ⌒O-Ph-CF₃ | 5-thia-6-oxo-16-(3-trifluoromethyl)phenoxy-17,18,19,20-tetranor-PGE₁ methyl ester | Rf 0.33 (EtOAc) | IR: $\nu$  3436, 2926, 2361, 1747, 1684, 1593, 1494, 1450, 1374, 1331, 1241, 1165, 1126, 1068, 1039 cm⁻¹ | 1, 2, 10 |
| 1 (ee) | ⌒⌒⌒COOCH₃ / H₃C-C(CH₃)-⌒⌒⌒ | 5-thia-6-oxo-16,16-dimethyl-PGE₁ methyl ester | Rf 0.12 (EtOAc:hexane = 2:1) | IR: $\nu$  3441, 2957, 2932, 2872, 1746, 1692, 1438, 1413, 1365, 1318, 1217, 1173, 1081, 1021 cm⁻¹ | 1, 2, 10 |

TABLE VI

| Example No. | R²¹\N⌒⌒R¹ / —R²—R³ | Name | TLC | mp or IR | Reference examples used |
|---|---|---|---|---|---|
| 1 (ff) | H\N⌒⌒⌒COOH / ⌒⌒⌒⌒ (CH₃) | 5-aza-6-oxo-17S,20-dimethyl-PGE₁ | Rf 0.07 (EtOAc:formic acid = 80:1) | IR: $\nu$  3400, 1700, 1220, 975 cm⁻¹ | 1, 2, 7 |

TABLE VI-continued

Structure (general):

O=C— with R²¹N substituent; cyclopentane ring with OH; side chain with R²—R³ and OH; R¹ substituent

| Example No. | —R²—R³ / R²¹N-CH₂-R¹ group | Name | TLC | mp or IR | Reference examples used |
|---|---|---|---|---|---|
| 1 (gg) | R²¹ = CH₃; N-CH₂CH₂CH₂-COOH; side chain with CH₃ branch (hexyl) | 5-methyl-5-aza-6-oxo-17S,20-dimethyl-PGE₁ | Rf 0.12 (EtOAc:formic acid = 80:1) | IR: $\nu$ 3350, 1730, 1620, 1400, 1225, 1160, 1070, 975 cm$^{-1}$ | 1, 2, 7 |
| 1 (hh) | R²¹ = H; N-CH₂CH₂CH₂-COOCH₃; n-hexyl side chain | 5-aza-6-oxo-PGE₁ methyl ester | Rf 0.36 (CH₂Cl₂:CH₃OH = 9:1) | IR: $\nu$ 3550~3100, 3000, 2950, 2930, 2850, 1720, 1680, 1440, 1410, 1370, 1260, 1190, 1065 cm$^{-1}$ | 1, 2, 7 |
| 1 (ii) | R²¹ = H; N-CH₂CH₂CH₂-COOH; cyclopropyl/ethano-ethyl side chain | 5-aza-6-oxo-16S,18S-ethano-20-ethyl-PGE₁ | Rf 0.25 (EtOAc:CH₃OH:acetic acid = 90:10:2) | IR: $\nu$ 3333, 2931, 2859, 1714, 1668, 1652, 1447, 1416, 1378, 1258, 1089, 1049 cm$^{-1}$ | 1, 2, 7 |

TABLE VII

| Example No. | Structure | Name | TLC | mp or IR | Reference examples used |
|---|---|---|---|---|---|
| 1 (jj) | cyclopentanone with O-CH₂C(O)O-(CH₂)₄-OH ester chain; HO-substituted alkene side chain with gem-dimethyl and n-butyl | 5-oxa-6-oxo-16,16-dimethyl-1-deoxo-PGE₁ | Rf 0.13 (EtOAc) | IR: $\nu$ 3402, 2958, 2933, 2872, 1740, 1470, 1363, 1244, 1191, 1079, 1047, 999, 973 cm$^{-1}$ | 1, 2, 3 |
| 1 (kk) | cyclopentanone with O-CH₂C(O)O-(CH₂)₄-OH; side chain with OH and OPh (phenoxy) | 5-oxa-6-oxo-16-phenoxy-17,18,19,20-tetranor-1-deoxo-PGE₁ | Rf 0.11 (EtOAc) | IR: $\nu$ 3392, 2923, 1732, 1600, 1588, 1495, 1456, 1396, 1358, 1245, 1174, 1079, 1042, 973 cm$^{-1}$ | 1, 2, 3 |
| 1 (ll) | cyclopentanone with O-CH₂C(O)O-(CH₂)₄-CONH-CH(COOH)-CH₂-Ph; side chain with HO and Me | 5-oxa-6-oxo-17S,20-dimethyl-PGE₁ N-(1R-carboxy-2-phenyl)ethylamide | Rf 0.1 (EtOAc:MeOH:AcOH = 95:5:2) | IR: $\nu$ 3351, 1735, 1653, 1541, 1456, 1192, 1079, 971 cm$^{-1}$ | 1, 2, 3, 4, 5, 11 |

FORMATION EXAMPLE 1

The following components were admixed and dried in conventional manner. Sufficient microcrystalline cellulose was added to obtain 10 g of mixture. After mixing well, the mixture was punched out in conventional manner to obtain 100 tablets each containing 30 µg of the active ingredient.

| | |
|---|---|
| α-cyclodextrin clathrate of 5-oxa-6-oxo- | 42 mg |

| -continued | |
|---|---|
| 17S,20-dimethyl-1-deoxo-PGE1 (3 mg) | |
| Magnesium sterate | 100 mg |
| Silicon dioxide | 20 mg |
| Talc | 10 mg |
| Cellulose calcium glycolate | 200 mg |

FORMATION EXAMPLE 2

6 mg of α-cyclodextrin clathrate of 5-oxa-6-oxo-17S,20-dimethyl-PGE1 methyl ester (0.5 mg) was dissolved in 300 ml of distilled water for injection. The solution was sterilized in conventional manner and placed in 3 ml portion in 5 ml ampoules to obtain 100 ampoules each containing 5 μg of the active ingredient.

FORMATION EXAMPLE 3

30 mg of 5-oxa-6-oxo-17S,20-dimethyl-PGE1 in 10 ml of chloroform was added to 100 ml of MCT (a mixture of triglycerides of fatty acids containing from 8 to 10 carbon atoms) and the solution was mixed well. After removing chloroform under reduced pressure, the residue was machine filled into 100 soft capsules each containing 30 μg of the active ingredient.

What is claimed is:

1. A 5-hetero-6-oxo-PGE derivative of the formula:

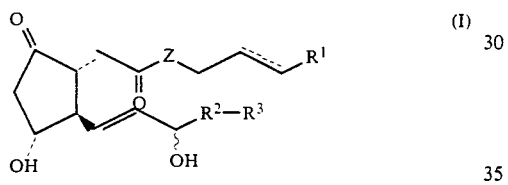

wherein $R^1$ is hydroxymethylcarbonyl, hydroxymethyl or a group of the formula:

CO—AA wherein AA is an amino acid-residue selected from the group consisting of glycine, alanine, valine, isoleucine, leucine, serine, threonine, proline, asparagine, glutamine, methionine, phenylalanine, tyrosine, aspartic acid and glutamic acid, Z is oxygen, sulfur or a group of the formula:

$NR^{21}$ wherein $R^{21}$ is hydrogen or $C_1$–$C_4$ alkyl;

$R^2$ is a single-bond or $C_1$–$C_4$ alkylene;

$R^3$ is $C_1$–$C_7$ alkyl, $C_4$–$C_7$ cycloalkylene which is unsubstituted or substituted by $C_1$–$C_7$ alkyl, phenyl which is unsubstituted or substituted by $C_1$–$C_4$ alkyl, halogen or trihalomethyl, or phenoxy which is unsubstituted or substituted by $C_1$–$C_4$ alkyl, halogen or trihalomethyl; and === is a single-bond or double-bond, with the proviso that when $R^2$ is a single bond, $R^3$ is not phenoxy which is unsubstituted or substituted by $C_1$–$C_4$ alkyl, halogen or trihalomethyl;

or a non-toxic salt or cyclodextrin clathrate thereof.

2. A compound of claim 1 wherein Z is oxygen.

3. A compound according to claim 1 wherein $R^1$ is hydroxymethylcarbonyl.

4. A compound according to claim 2 wherein $R^1$ is hydroxymethyl carbonyl.

5. A compound according to claim 1 wherein $R^1$ is hydroxymethyl.

6. A compound according to claim 2 wherein $R^1$ is hydroxymethyl.

7. A compound according to claim 1 wherein $R^1$ is a group of the formula CO—AA.

8. A compound according to claim 2 wherein $R^1$ is a group of the formula CO—AA.

9. A compound according to claim 1 which is 5-oxa-6-oxo-17S,20-dimethyl-2-glycolonyl-2-decarboxy-PGE1.

10. A compound according to claim 1 which is a 5-hetero-6-oxo-PGE derivative selected from the group consisting of:

5-oxa-6-oxo-17S,20-dimethyl-1-deoxo-PGE1,
5-oxa-6-oxo-16S,18S-ethano-20-ethyl-1-deoxo-PGE1,
5-oxa-6-oxo-16,16-dimethyl-1-deoxo-PGE1 and
5-oxa-6-oxo-16-phenoxy-17,18,19,20, -tetranor-1-deoxo-PGE1.

11. A compound according to claim 1 which is a 5-hetero-6-oxo-PGE 5-hetero-6-oxo-PGE derivative selected from the group consisting of:

5-oxa-6-oxo-17S,20-dimethyl-PGE1 N-(1S-carboxy-3-methyl)butylamide,
5-oxa-6-oxo-PGE1 N-(1R-carboxy-2-phenyl)ethylamide and
5-oxa-6-oxo-17S,20-dimethyl-PGE1 N-(1R-carboxy-2-phenyl)ethylamide.

12. A hetero-6-oxo-PGE derivative of the formula:

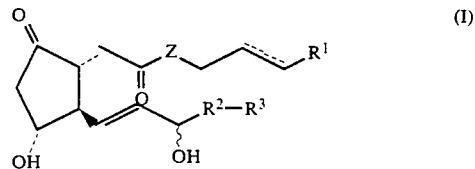

wherein $R^1$ is a group of the formula:

$COOR^{11}$ wherein $R^{11}$ is hydrogen, $C_1$–$C_{14}$ alkyl, $C_1$–$C_7$ cycloalkyl which is unsubstituted or substituted by $C_1$–$C_7$ alkyl, adamantyl, a group of the formula:

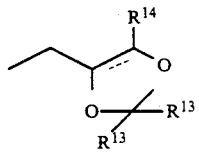

wherein $R^{12}$ and $R^{13}$ each, independently is halogen $C_1$–$C_4$ alkyl or phenyl, or $R^{12}$ or $R^{13}$, taken together, are oxo or a spirocyclopentane or spirocyclohexane ring, $R^{14}$ is hydrogen or $C_1$–$C_4$ alkyl, and=== is a single-bond or a double-bond, a group of the formula:

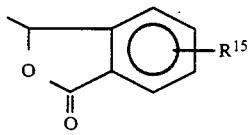

wherein $R^{15}$ is hydrogen, $C_1-C_4$ alkyl, halogen or trihalomethyl,
a group of the formula:

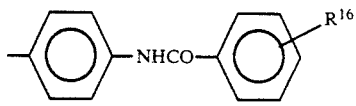

wherein $R^{16}$ is hydrogen, $C_1-C_4$ alkyl, halogen or trihalomethyl,
a group of the formula:

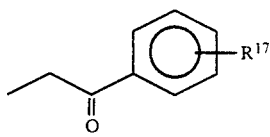

wherein $R^{17}$ is hydrogen, $C_1-C_4$ alkyl, halogen or trihalomethyl,
a residue or steroids selected from the group consisting of cholesterol and cholic acid, $C_3-C_{10}$ alkanoyloxyalkyl or $C_3-C_8$ alkoxycarbonyloxyalkyl;
Z is oxygen;
$R^2-R^3$ represents a 2-methylhexyl, 1,1-dimethylpentyl or 1-methylpentyl group; and
 is a single-bond or a double bond;
or a non-toxic salt of cyclodextrin clathrate thereof.

13. A compound according to claim 12, which is 5-oxa-6-oxo-16-methyl-PGE$_1$.

14. A 5-hetero-6-oxo-PGE derivative of the formula:

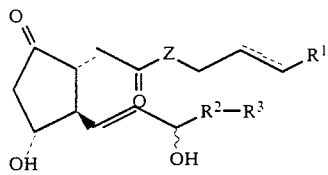 (I)

wherein $R^1$ is a group of the formula:

COOR$^{11}$ wherein $R^{11}$ is hydrogen, $C_1-C_{14}$ alkyl, $C_4-C_7$ cycloalkyl which is unsubstituted or substituted by $C_1-C_7$ alkyl, adamantyl,
a group of the formula:

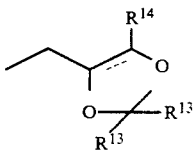

wherein $R^{12}$ and $R^{13}$ each, independently, is hydrogen, $C_1-C_4$ alkyl or phenyl, or $R^{12}$ and $R^{13}$, taken together, are oxo or a spirocyclopentane or spirocyclohexane ring, $R^{14}$ is hydrogen or $C_1-C_4$ alkyl and  is a single-bond or a double bond,
a group of the formula:

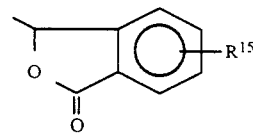

wherein $R^{15}$ is hydrogen, $C_1-C_4$ alkyl, halogen or trihalomethyl,
a group of the formula:

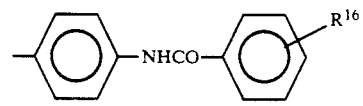

wherein $R^{16}$ is hydrogen, $C_1-C_4$ alkyl, halogen or trihalomethyl,
a group of the formula:

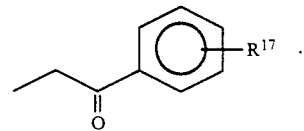

wherein $R^{17}$ is hydrogen, $C_1-C_4$ alkyl, halogen or trihalomethyl,
a residue of steroids selected from the group consisting of cholesterol and cholic acid, $C_3-C_{10}$ alkanoyloxyalkyl or $C_3-C_8$ alkoxycarbonyloxyalkyl;
Z is sulfur;
$R^2$ is a single-bond or $C_1-C_4$ alkylene;
$R^3$ is $C_1-C_7$ alkyl, $C_4-C_7$ cycloalkyl which is unsubstituted or substituted by $C_1-C_7$ alkyl, phenyl which is unsubstituted or substituted by $C_1-C_4$ alkyl, halogen or trihalomethyl or phenoxy which is unsubstituted or substituted by $C_1-C_4$ alkyl, halogen or trihalomethyl;
 is a single-bond or a double-bond,
with the proviso that when $R^2$ is a single-bond, $R^3$ is not phenoxy which is unsubstituted or substituted by $C_1-C_4$ alkyl, halogen or trihalomethyl;
or a non-toxic salt or cyclodextrin clathrate thereof.

15. A compound according to claim 14 which is a 5-hetero-6-oxo-PGE derivative selected from the group consisting of:
5-thia-6-oxo-17S,20-dimethyl-PGE1 methyl ester,
5-thia-6-oxo-16-phenoxy-17,18,19,20-tetranor-PGE1 methyl ester,
5-thia-6-oxo-16S,18S-ethano-20-ethyl-PGE1 methyl ester,
5-thia-6-oxo-16-(3-trifluoromethyl)phenoxy-17,18,19,20-tetranor-PGE1 methyl ester and
5-thia-6-oxo-16,16-dimethyl-PGE1 methyl ester.

16. A hetero-6-oxo-PGE derivative of the formula:

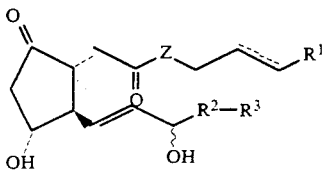 (I)

wherein $R^1$ is a group of the formula:

COOR$^{11}$ wherein R$^{11}$ is hydrogen, C$_1$–C$_{14}$ alkyl, C$_4$–C$_7$ cycloalkyl which is unsubstituted or substituted by C$_1$–C$_7$ alkyl, adamantyl,
a group of the formula:

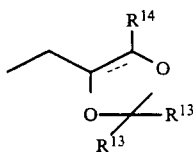

wherein R$^{12}$ and R$^{13}$ each, independently is halogen, C$_1$–C$_4$ alkyl or phenyl, or R$^{12}$ and R$^{13}$, taken together, are oxo or a spirocyclopentane or spirocyclohexane ring, R$^{14}$ is hydrogen or C$_1$–C$_4$ alkyl, and$\doteq$is a single-bond or a double-bond,
a group of the formula:

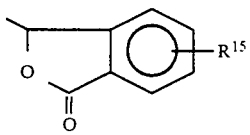

wherein R$^{15}$ is hydrogen, C$_1$–C$_4$ alkyl, halogen or trihalomethyl,
a group of the formula:

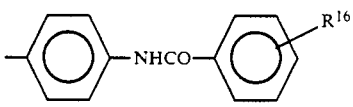

wherein R$^{16}$ is hydrogen, C$_1$–C$_4$ alkyl, halogen or trihalomethyl,
a group of the formula:

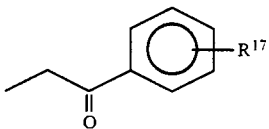

wherein R$^{17}$ is hydrogen, C$_1$–C$_4$ alkyl, halogen or trihalomethyl;
a residue of steroids selected from the group consisting of cholesterol and cholic acid, C$_3$–C$_{10}$ alkanoyloxyalkyl or C$_3$–C$_8$ alkoxycarbonyloxyalkyl;
Z is oxygen, sulfur or a group of the formula:

NR$^{21}$ wherein R$^{21}$ is hydrogen or C$_1$–C$_4$ alkyl;
R$^2$ is a single-bond or C$_1$–C$_4$ alkylene;
R$^3$ is C$_4$–C$_7$ cycloalkyl which is unsubstituted or substituted by C$_1$–C$_7$ alkyl, phenyl which is unsubstituted or substituted by C$_1$–C$_4$ alkyl, halogen or trihalomethyl, or phenoxy which is unsubstituted or substituted by C$_1$–C$_4$ alkyl, halogen or trihalomethyl;
$\doteq$is a single-bond or a double-bond;

with the proviso that when R$^2$ is a single-bond, R$^3$ is not phenoxy which is unsubstituted or substituted by C$_1$–C$_4$ alkyl, halogen or trihalomethyl, or
a non-toxic salt or cyclodextrin clathrate thereof.

17. A compound of claim 16 wherein Z is oxygen.
18. A compound according to claim 16 which is 5-aza-6-oxo-16S,18S-ethano-20-ethyl-PGE1.
19. A 5-hetero-6-oxo-PGE derivative selected from the group consisting of:
5-oxa-6-oxo-17S,20-dimethyl-PGE1,
5-oxa-6-oxo-17S,20-dimethyl-PGE1 cholesterol ester,
5-oxa-6-oxo-17S,20-dimethyl-PGE1 methyl ester,
5-oxa-6-oxo-17S,20-dimethyl-PGE1 4-(benzoylamino) phenyl ester,
5-oxa-6-oxo-17S,20-dimethyl-PGE1 hexyl ester,
5-oxa-6-oxo-17S,20-dimethyl-PGE1 decyl ester,
5-oxa-6-oxo-17S,20-dimethyl-PGE1 isopropyl ester,
5-oxa-6-oxo-17S,20-dimethyl-PGE1 adamantyl ester,
5-oxa-6-oxo-17S,20-dimethyl-PGE1 pivaloyloxymethyl ester,
5-oxa-6-oxo-17S,20-dimethyl-2,3-dehydro-PGE1 methyl ester,
5-oxa-6-oxo-17S,20-dimethyl-PGE1 2,2-dimethyl-1,2-dioxoran-4-ylmethyl ester,
5-oxa-6-oxo-17S,20-dimethyl-PGE1 1-(ethoxycarbonyloxy)ethyl ester,
5-oxa-6-oxo-17S,20-dimethyl-PGE1 5-methyl-2-oxo-1,3-dioxorene-4-ylmethyl ester,
5-oxa-6-oxo-17S,20-dimethyl-PGE1 3-phthalidyl ester,
5-oxa-6-oxo-17S,20-dimethyl-PGE1 4-bromobenzoylmethyl ester,
5-oxa-6-oxo-17S,20-dimethyl-PGE1 benzoylmethyl ester,
5-oxa-6-oxo-17S,20-dimethyl-PGE1 ethyl ester,
5-oxa-6-oxo-16,16-dimethyl-PGE1 methyl ester,
5-oxa-6-oxo-16S,18S-ethano-20-ethyl-PGE1,
5-oxa-6-oxo-16S,18S-ethano-20-ethyl-PGE1 methyl ester,
5-oxa-6-oxo-16-phenoxy-17,18,19,20-tetranor-PGE1 methyl ester and
5-oxa-6-oxo-16-(3-trifluoromethylphenoxy)-17,18,19,20-tetranor-PGE1 methyl ester.

20. A pharmaceutical composition for the prevention and treatment of cytodamage which comprises, as active ingredient, a pharmaceutically effective amount of the derivative of 5-hetero-6-oxo-PGE of claim 1 and a pharmaceutically acceptable carrier.
21. A pharmaceutical composition for the prevention and treatment of cytodamage which comprises, as active ingredient, a pharmaceutically effective amount of the derivative of 5-hetero-6-oxo-PGE of claim 14 and a pharmaceutically acceptable carrier.
22. A pharmaceutical composition for the prevention and treatment of cytodamage which comprises, as active ingredient, a pharmaceutically effective amount of the derivative of 5-hetero-6-oxo-PGE of claim 16 and a pharmaceutically acceptable carrier.
23. A pharmaceutical composition for the prevention and treatment of cytodamage which comprises, as active ingredient, a pharmaceutically effective amount of the derivative of 5-hetero-6-oxo-PGE of claim 12 and a pharmaceutically acceptable carrier.
24. A method for the prevention and treatment of cytodamage in a patient, which comprises administering to the patient a pharmaceutically effective amount of the 5-hetero-6-oxo-PGE derivative of claim 1, in the form of a non-toxic salt or cyclodextrin clathrate thereof.

25. A method for the prevention and treatment of cytodamage in a patient, which comprises administering to the patient a pharmaceutically effective amount of the 5-hetero-6-oxo-PGE derivative of claim 14, in the form of a non-toxic salt or cyclodextrin clathrate thereof.

26. A method for the prevention and treatment of cytodamage in a patient, which comprises administering to the patient a pharmaceutically effective amount of the 5-hetero-6-oxo-PGE derivative of claim 16, in the form of a non-toxic salt or cyclodextrin clathrate thereof.

27. A method for the prevention and treatment of cytodamage in a patient, which comprises administering to the patient a pharmaceutically effective amount of the 5-hetero-6-oxo-PGE derivative of claim 12, in the form of a non-toxic salt or cyclodextrin clathrate thereof.

* * * * *